(12) United States Patent
Betsill

(10) Patent No.: US 8,236,246 B2
(45) Date of Patent: Aug. 7, 2012

(54) GAS SENSITIVE APPARATUS

(75) Inventor: Harry Edwards Betsill, Parkton, MD (US)

(73) Assignee: E I du Pont de Nemours and Company, Wilmington, DE (US)

( * ) Notice: Subject to any disclaimer, the term of this patent is extended or adjusted under 35 U.S.C. 154(b) by 1244 days.

(21) Appl. No.: 11/241,452

(22) Filed: Sep. 29, 2005

(65) Prior Publication Data

US 2006/0108220 A1      May 25, 2006

Related U.S. Application Data

(60) Provisional application No. 60/617,246, filed on Oct. 7, 2004.

(51) Int. Cl.
*G01N 31/12* (2006.01)

(52) U.S. Cl. ........ 422/94; 73/23.2; 73/861.08; 204/600; 250/370.01

(58) Field of Classification Search .................. 204/600; 73/861.08; 250/370.01; 422/94
See application file for complete search history.

(56) References Cited

U.S. PATENT DOCUMENTS

| | | |
|---|---|---|
| 4,007,435 A | 2/1977 | Tien |
| 4,151,503 A | 4/1979 | Cermak et al. |
| 4,225,842 A | 9/1980 | Schlesselman et al. |
| 4,234,542 A | 11/1980 | Romine |
| 4,347,732 A | 9/1982 | Leary |
| 4,387,359 A | 6/1983 | Tien et al. |
| 4,457,161 A | 7/1984 | Iwanaga et al. |
| 4,535,316 A | 8/1985 | Wertheimer et al. |
| 4,542,640 A | 9/1985 | Clifford |
| 4,770,760 A | 9/1988 | Noda et al. |
| 4,847,783 A | 7/1989 | Grace |
| 4,911,982 A | 3/1990 | Rice |
| 5,132,541 A * | 7/1992 | Conrads et al. .......... 250/370.01 |
| 5,239,483 A | 8/1993 | Weir |
| 5,426,934 A | 6/1995 | Hunt |
| 5,427,740 A | 6/1995 | Coles |
| 5,554,273 A | 9/1996 | Demmin et al. |
| 5,571,401 A | 11/1996 | Lewis |
| 5,605,612 A | 2/1997 | Park et al. |
| 5,630,920 A | 5/1997 | Friese et al. |
| 5,731,510 A | 3/1998 | Jones et al. |
| 5,736,028 A | 4/1998 | Hjortsberg et al. |
| 5,776,601 A | 7/1998 | Fournier et al. |
| 5,832,411 A | 11/1998 | Schatzmann |
| 5,879,526 A | 3/1999 | Dietz et al. |
| 5,952,555 A | 9/1999 | Mobius |

(Continued)

FOREIGN PATENT DOCUMENTS

DE         44 08 361 A1      9/1995

(Continued)

OTHER PUBLICATIONS

Brent T. Marquis et. al., A Semiconducting Metal Oxide Sensor Array for the Detection of NOx and NH3, Sensors and Actuators B, 2001, pp. 100-110, vol. 77.

(Continued)

*Primary Examiner* — In Suk Bullock
*Assistant Examiner* — Robert Eom

(57) ABSTRACT

Disclosed herein is a gas sensitive apparatus that is useful in view of its applicability to the detection or quantitative determination of individual gases present in a gas mixture, and is advantageous in view of its compact size, and its low power consumption.

10 Claims, 4 Drawing Sheets

U.S. PATENT DOCUMENTS

| | | | |
|---|---|---|---|
| 6,012,282 | A | 1/2000 | Kato et al. |
| 6,082,176 | A | 7/2000 | Kondo et al. |
| 6,084,418 | A | 7/2000 | Takami et al. |
| 6,085,576 | A | 7/2000 | Sunshine et al. |
| 6,101,865 | A | 8/2000 | Meixner |
| 6,109,095 | A | 8/2000 | Addiego |
| 6,170,318 | B1 | 1/2001 | Lewis |
| 6,235,243 | B1 | 5/2001 | Fleischer et al. |
| 6,481,264 | B1 | 11/2002 | Williams |
| 6,849,239 | B2 | 2/2005 | Morris |
| 6,890,715 | B1 | 5/2005 | Lewis |
| 6,960,476 | B2 | 11/2005 | Morris |
| 7,231,290 | B2 | 6/2007 | Steichen |
| 7,763,208 | B2 | 7/2010 | Steichen |
| 8,043,566 | B2 | 10/2011 | Morris |
| 2002/0017467 | A1 | 2/2002 | Ando |
| 2004/0013571 | A1 | 1/2004 | Morris |
| 2005/0063873 | A1 | 3/2005 | Morris |

FOREIGN PATENT DOCUMENTS

| | | |
|---|---|---|
| DE | 44 08 504 A1 | 9/1995 |
| WO | WO 00/00808 A2 | 1/2000 |

OTHER PUBLICATIONS

S.W. Moore et. al., A Modified Multilayer Perceptron Model for Gas Mixture Analysis, Sensors and Actuators B, 1993, pp. 344-348.

G. Huyberechts et. al., Simultaneous Quantification of Carbon Monoxide and Methane in Humid Air Using a Sensor Array and an Artificial Neural Network, Sensors and Actuators B, 1997, pp. 123-130, vol. 45.

Kazimierz Brudzewski et. al., Gas Analysis System Composed of a Solid-State Sensor Array and Hybrid Neural Network Structure, Sensors and Actuators B, 1999, pp. 38-46, vol. 55.

P.C. Jurs et. al., Computational Methods for the Analysis of Chemical Sensor Array Data From Volatile Analytes, Chem. Rev., 2000, pp. 2649-2678, vol. 100.

Keith J. Albert et. al., Cross-Reactive Chemical Sensor Arrays, Chem. Rev., 2000, pp. 2595-2626. vol. 100.

H. Meixner et. al., Metal Oxide Sensors, Sensors and Actuators B, 1996, p. 198-202, vol. 33.

J. Getino et. al., Integrated Sensor Arrays for Gas Analysis in Combustion Atmospheres, Sensors and Actuators B, 1996, pp. 128-133, vol. 33.

Corrado Di Natale et. al., Study of the Effect of the Sensor Operating Temperature on SNO2-Based Sensor Array Performance, Sensors and Actuators B, 1995, pp. 187-191, vol. 23.

Gardner et. al., Solid State Chemical and Biochemical Sensors, Advances in Science and Technology, 1999, pp. 335-345, vol. 26.

Antonio Pardo et. al., Nonlinear Inverse Dynamic Models of Gas Sensing Systems Based on Chemical Sensor Arrays for Quantitative Measurements, IEEE Transaction of Instrumentation and Measurement, 1998, pp. 644-651, vol. 47.

B.S. Hoffheins et. al., Performance of Simpllfied Chemical Sensor Arrays in a Neural Network-Based Analytical Instrument, Analusis, 1992, pp. 201-207, vol. 20.

H. Meixner et. al., Chemosensors for Motor Management Systems of the Future, Fresenius J. Anal. Chem., 1994, pp. 536-541, vol. 348.

Corrado Di Natale et. al., Performance Evaluation of an SNO2-Based Sensor Array for the Quantitative Measurement of Mixtures of H2S and NO2, Sensors and Actuators B, 1994, pp. 217-224, vol. 20.

* cited by examiner

GAS SENSITIVE APPARATUS

This application claims the benefit of U.S. Provisional Application No. 60/617,246, filed on Oct. 7, 2004, which is incorporated in its entirety as a part hereof for all purposes.

TECHNICAL FIELD

This invention relates to a gas-sensitive apparatus for gas analysis, which apparatus is particularly, but not exclusively, useful for the analysis of automotive exhaust emissions, or the emissions from other internal combustion engines. The apparatus is particularly advantageous in view of its applicability to the detection or quantitative determination of individual gases present in a mixture, its compact size, and its low power consumption.

BACKGROUND

In an automotive engine, it is advantageous to be able to detect the presence or concentration of the various components in the exhaust gas stream. Such analysis and measurement can be used for controlling the operation of the engine, with a view toward optimizing the amounts of injected fuel and air. If the engine can be provided with an optimal composition of the fuel/air mixture during all operating conditions, the fuel consumption and the harmful emissions from the engine can be minimized. In addition to engine control, gas analysis and measurement can also play a role in the diagnosis of the automotive catalytic converter. The fuel and oxygen levels in the exhaust gas stream should generally lie within certain ranges for the optimum performance of the catalytic converter.

A variety of gases are typically present in an automotive engine exhaust stream, including, for example, oxygen, nitrogen oxide compounds (NOx), carbon monoxide, sulfur oxides (SOx), hydrogen sulfide ($H_2S$), hydrocarbons, ammonia, hydrogen and water. Numerous products are known that are intended to analyze a stream of gas using a gas sensor device. A typical gas sensor device employs as sensor element(s) one or more chemo/electro-active materials, each of which is a material that will exhibit a change in an electrical property upon exposure to a gas.

A complicating factor in the process of analyzing and measuring the wide variety of gaseous components in a mixture such as exhaust gas is that the signal from one particular sensor element can be influenced by its exposure to gases other the gas(es) for which its signal is intended to serve as the desired analytical data. For example, a material selected as a sensor to respond to NOx, apart from detecting the presence or concentration of a nitrogen oxide compound, may also be sensitive to the presence of oxygen or a hydrocarbon. This difficulty has been addressed by simultaneously using a plurality of different types of sensor elements to generate enough data to permit separation of those signals that are accurately reflective of the presence of an analyte gas from those that are the unavoidable result of the cross-sensitivity of the different sensor elements to the total population of gases.

A gas sensor device constructed with a plurality of different sensor elements to address such problem of cross-sensitivity may, however, be subject to size limitations depending on the nature of its deployment. If the gas sensor device will be used for automotive purposes, it will be subject to very strict and demanding size limitations. Many currently known automotive gas sensors, such as that described for example in U.S. Pat. No. 5,556,526, must be small enough to pass through a circle having a diameter of no more than 100 mm, if not smaller. On-board automotive diagnostics is, however, not the only use for a gas analyzer having compact size as hand-held devices for monitoring all varieties of toxic and hazardous gaseous materials are becoming increasingly important.

When constructing a size-limited gas sensor, there is consequently an inevitable tension between the desire to utilize as many different sensor elements in the device as possible, and the need for the sensor device to meet the applicable size limitation. Each separate sensor element raises considerations of not only the space occupied by the element itself, but the location and arrangement of the conductors, connectors and cabling that carry the input and output pulses and signals necessary to operate all of the sensor elements that are contained in the sensor device. This has resulted in a need to develop components for the device, such as a gas sensitive apparatus, that enable increasing the number of sensor elements that can be used in the sensor device while maintaining the size of the device within permitted limits.

The present invention meets this need as it provides a gas sensitive apparatus for use as a component in a gas sensor device that permits the construction of a device containing a desirably high number of sensor elements and yet meeting virtually all applicable size limitations for use for automotive purposes or in other desired industrial settings. The use of the gas sensitive apparatus of this invention in a gas sensor device is, of course, not limited to the automotive industry.

One particular advantage of this invention is that it provides, in a gas sensitive apparatus, a space-saving arrangement for a large number of sensor elements, and the electrodes (such as printed electrodes) that are associated therewith. Another advantage of this invention is that it provides in a gas sensitive apparatus a space-saving arrangement for a plurality of conductors that are sufficient in number to carry pulse and signal inputs and outputs to and from the many sensor elements. By incorporating a large number of sensor elements in a compact, small-sized gas sensitive apparatus, the present invention enables the discrimination of very low concentrations of a wide variety of components in a gas mixture under conditions of virtually any size limitation. The gas sensitive apparatus is incorporated into a gas sensor device that is installed in an automotive vehicle or any other desired type of industrial equipment. These and other advantages are more particularly described below.

SUMMARY OF VARIOUS EMBODIMENTS OF THE INVENTION

One embodiment of this invention is a gas sensitive apparatus that may be passed through a circle having a diameter of no more than about 100 mm; and that includes (a) four or more sensor elements, and (b) two or more electrodes that each contacts two or more sensor elements.

Another embodiment of this invention is a gas-sensitive apparatus that includes (a) four or more sensor elements, (b) a first electrode that contacts at least one member of a first group of sensor elements, and (c) a second electrode that contacts at least one member of the first group of sensor elements and at least one member of a second group of sensor elements, wherein no member of the first group of sensor elements is a member of the second group of sensor elements.

Figure 1:
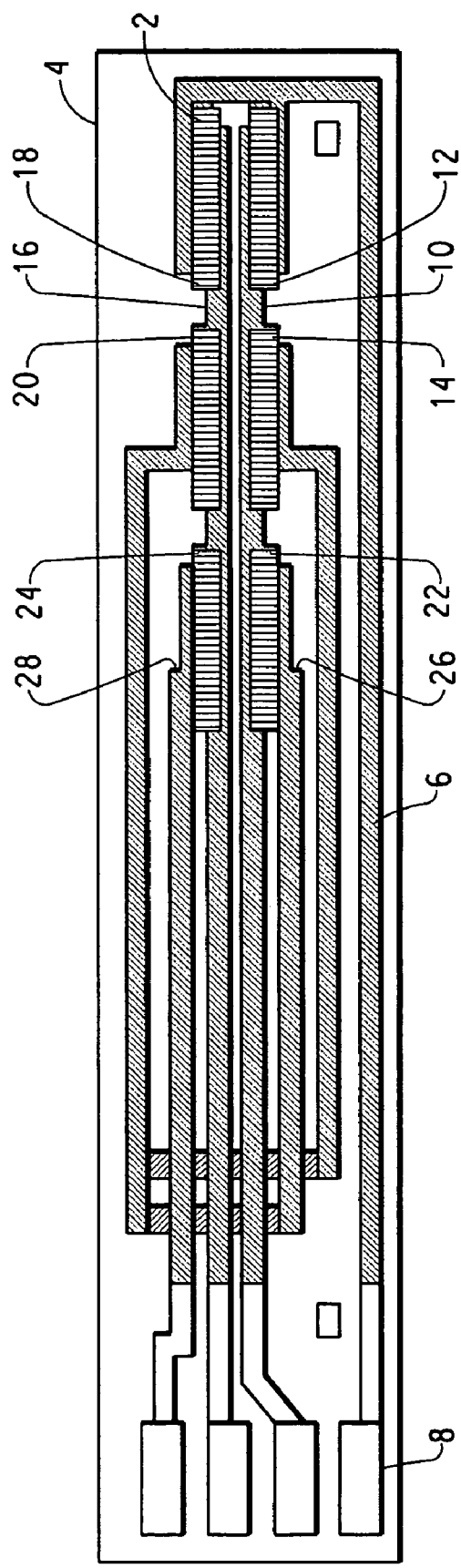
FIG. 1 is a schematic drawing of a multiplexed circuit connecting electrodes to sensor elements.
Figure 2:
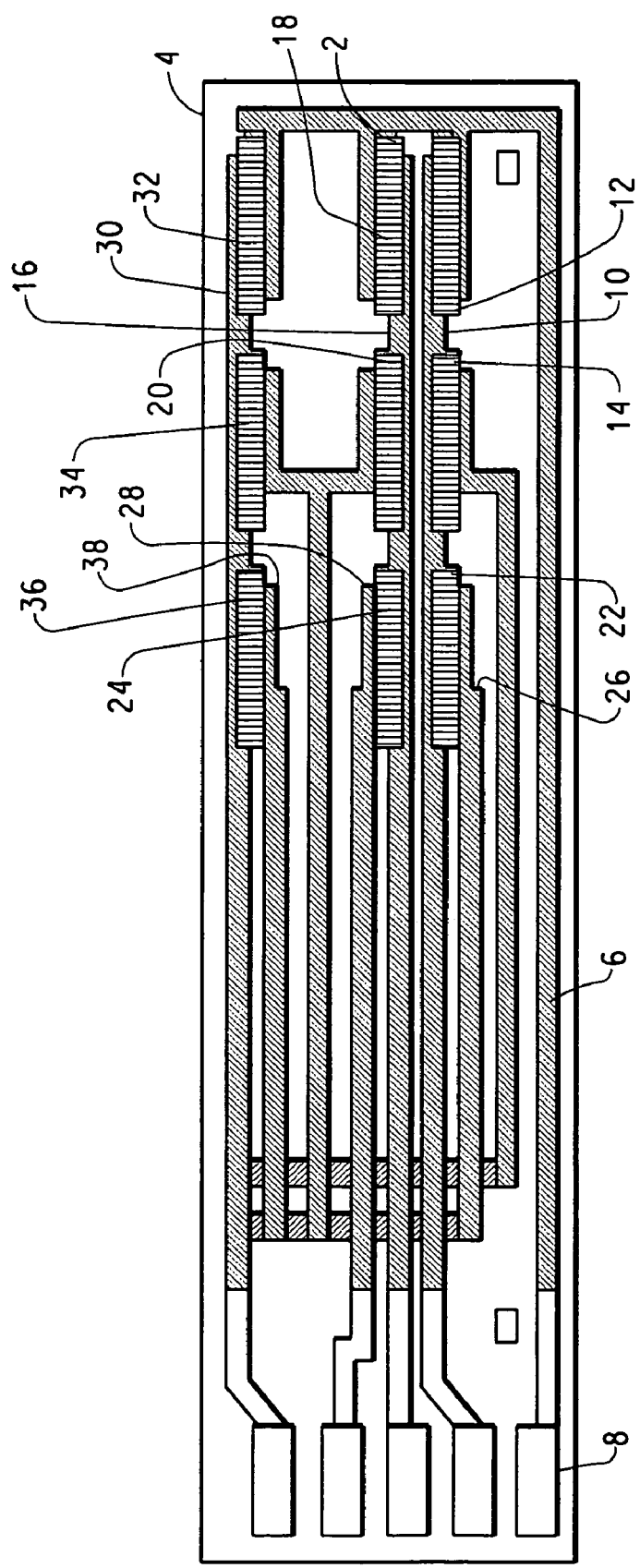
FIG. 2 is a schematic drawing of a multiplexed circuit connecting electrodes to sensor elements.
Figure 3:
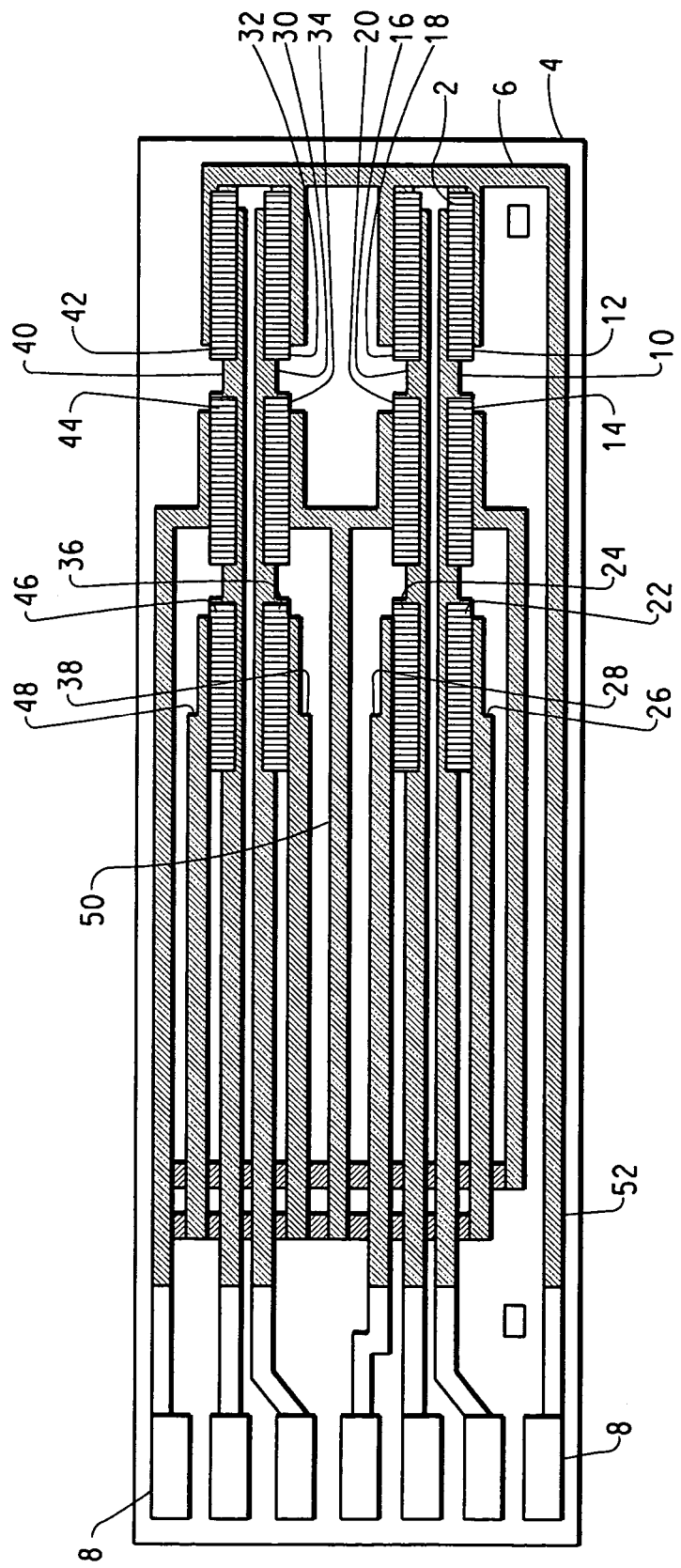
FIG. 3 is a schematic drawing of a multiplexed circuit connecting electrodes to sensor elements.

The same numbering for the features shown in FIG. 1 is continued in FIG. 2 where those same features are also shown in FIG. 2. The same numbering for the features shown in FIGS. 1 and 2 is continued in FIG. 3 where those same features are also shown in FIG. 3.

DETAILED DESCRIPTION

One embodiment of this invention is an apparatus for analyzing a mixture of gases, such as those contained in the exhaust gas of an internal combustion engine, wherein the apparatus may contain a plurality of sensor elements. The sensor elements may be mounted on a substrate such as a unitary body or a multi-layer laminate for detecting specific gases contained in the mixture, and generating signals based thereon. A substrate that is a unitary body is fabricated from a material such as alumina or zirconia as one solid piece of stock and is not fabricated by building up a plurality of discrete layers. A multi-layered laminate by contrast is fabricated by the assembly of a plurality of layers that are bonded together by treatment with heat and pressure. The substrate is typically planar in shape such that its cross section forms a rectangle in which the length of one dimension exceeds the other by 500% or more. The substrate may have other shapes, however, such that its cross section forms a rectangular rectangle in which the length of one dimension exceeds the other by less 500%, or the cross section has a trapezoidal, circular or oval shape.

In the gas sensitive apparatus, multiple gas sensor elements are used, which may constitute an array of individually electrically responsive solid state sensor elements mounted in relation to the gas input and output means so that an input flow of the gas mixture is passed over all the gas sensor elements substantially simultaneously. It is preferred, but not required, that at least one sensor element is provided for each one of the individual gases in the mixture to be analyzed. As noted above, however, additional sensor elements are also provided to cross check the signals resulting from the sensitivity of an individual element to more than one gas, and this may require a large number of sensor elements. The apparatus may also include heater for heating the substrate, such as a heating plate or wire mounted on or in the substrate. The heater is powered by a voltage source connected to the heating plate or wire.

Electrical conductivity changes in the sensor elements are caused by electrochemical interactions of the solid surfaces of the sensor elements with adsorbed gas species. The sensor elements may, for example, be prepared from metal oxide semiconductors. Electrical signals resulting from the interaction of gas and sensor surface are extracted as outputs and processed by an analyzer to detect the presence or concentration of various gaseous components in the mixture. Those determinations or computations are achieved by means of a look-up table or by an algorithm-controlled calculator function, or a more sophisticated deconvolution or neural network technique.

By placing a large number of sensor elements on one or more surfaces of a substrate, by multiplexing the pulse and signal input and output lines, and by providing a common amplifier unit and analyzer unit, an analysis of the different gas components in a gas mixture is made possible with a suitably small sensor device. The small size of the apparatus of this invention permits the sensor device to be placed close enough to the source from which the gas is generated that there is no significant change in the composition of the gas mixture between the time at which it is generated and the time at which it contacts the gas sensitive apparatus that is part of the sensor device.

A large number of sensor elements in the apparatus of this invention are accommodated by a multiplexed, space-saving layout of the sensor elements and the electrodes through which pulses and signals flow to and from the sensor elements. The sensor elements may be prepared from chemo/electro-active materials, as described below, and may be placed on one or more surfaces of the substrate. The electrodes may be prepared from metals such as gold, platinum or palladium or a mixture of two or more thereof, and may be placed on or within the substrate. Sensor elements and electrodes on the surface of a substrate may be applied by any of a variety of printing techniques as described below. Electrodes may be placed within a substrate by providing layers of "green" tape, one or more of which contain electrodes, and laminating the layers together to form a multi-layer laminate.

One particular embodiment of a space-saving layout of sensor elements and electrodes may be seen in FIG. 1. A plurality of sensor elements 2 is provided on a substrate 4. A plurality of electrodes 6 connects the various sensor elements 2 with contact terminals 8. Electrodes are available to enable completion of an electrical circuit through each sensor element. The contact terminals make contact with conductors (not shown) to enable passing electrical pulses to, and receiving signals from, the various sensor elements 2. The signals are routed to a microprocessor for handling as described below.

Where because of multiplexing, electrodes are shown crossing each other, that is accomplished by a dielectric layer in between the crossovers.

The gas sensitive apparatus of this invention may be passed through a circle having a diameter of no more than about 100 mm, preferably no more than about 50 mm, more preferably no more than about 25 mm, and most preferably no more than about 18 mm.

In one embodiment, the apparatus may, for example, have four or more sensor elements, and two or more electrodes that each contacts two or more sensor elements. For example, Electrode A 10 contacts Sensor Elements A-1 12 and A-2 14, and Electrode B 16 contacts Sensor Elements B-1 18 and B-2 20. As may be seen, Electrodes A 10 and B 12 each contacts different sensor elements.

Sensor Element A-3 22 and Sensor Element B-3 24 are individually optional. Although shown in FIG. 1, either or both may or may not be included in the apparatus depending on the estimated difficulty of the gas analysis task at hand, which will indicate the number of sensor elements needed to accomplish resolution of the gas mixture at the desired level of detail. If Sensor Elements A-3 22 and B-3 24 are present as shown, Electrode C 26 and Electrode D 28 will also be present as shown. If either or both of Sensor Elements A-3 22 and B-3 24 are not present, the corresponding electrode will also not be present. If Sensor Element A-3 22 is present as shown, a circuit may be completed through it using Electrodes A 10 and C 26, and a circuit may be completed through other sensor elements in an analogous manner using the electrodes adjacent to them, respectively, as shown in the various drawings hereof.

In the embodiment, in which Sensor Element A-3 22 is present, it may be seen that Electrode A 10 contacts three sensor elements. Similarly, in the embodiment, in which Sensor Element B-3 24 is present, it may be seen that Electrode B 16 contacts three sensor elements. Electrodes A 10 and B 16 in those cases contact different sensor elements.

An alternative embodiment is shown in FIG. 2, in which the apparatus contains sensor elements and electrodes in addition to those described in the embodiment as shown in FIG. 1. The same numbering for the features shown in FIG. 1 is continued in FIG. 2 where those same features are also shown in FIG. 2. In FIG. 2, Electrode E 30 contacts Sensor Elements E-1 32 and E-2 34, and is thus a third electrode that contacts two or more sensor elements. Electrode E 30 contacts different sensor elements that either of Electrodes A 10 and B 16.

Sensor Element E-3 36 is optional, and, although shown in FIG. 2, may or may not be included in the apparatus. If Sensor Element E-3 36 is present as shown, Electrode F 38 will also be present as shown. If Sensor Element E-3 36 is not present, Electrode F 38 will also not be present. If Sensor Element E-3 36 is present as shown, Electrode E 30 is a third electrode that contacts three sensor elements. Electrode E 30 in such instance also contacts different sensor elements that either of Electrodes A 10 and B 16.

A further alternative embodiment is shown in FIG. 3, in which the apparatus contains sensor elements and electrodes in addition to those described in the embodiment as shown in FIG. 2. The same numbering for the features shown in FIG. 2 is continued in FIG. 3 where those same features are also shown in FIG. 3. In FIG. 3, Electrode G 40 contacts Sensor Elements G-1 42 and G-2 44, and is thus a fourth electrode that contacts two or more sensor elements. Electrode G 40 contacts different sensor elements that any of Electrodes A 10, B 16 and E 30.

Sensor Element G-3 46 is optional, and, although shown in FIG. 3, may or may not be included in the apparatus. If Sensor Element G-3 46 is present as shown, Electrode H 48 will also be present as shown. If Sensor Element G-3 46 is not present, Electrode H 48 will also not be present. If Sensor Element G-3 46 is present as shown, Electrode G 40 is a fourth electrode that contacts three sensor elements. Electrode G 40 in such instance also contacts different sensor elements that any of Electrodes A 10, B 16 and E 30.

Referring to FIG. 2, it may be seen that Electrode J 50 contacts Sensor Elements B-2 20 and E-2 34, and that Electrode K 52 contacts Sensor Elements A-1 12, B-1 18 and E-1 32. Referring to FIG. 3, it may be seen that Electrode K 52 contacts Sensor Elements A-1 12, B-1 18, E-1 32 and G-1 42. Electrodes A 10, B 16, E 30, G 40, J 50 and K 52 may thus each be described as an electrode that contacts two or more sensor elements. Moreover, Electrodes A 10, B 16, E 30, G 40 and K 52 may each be described as an electrode that contacts three or more sensor elements, and Electrode K 52 may be described as an electrode that contacts four sensor elements.

Figure 4:
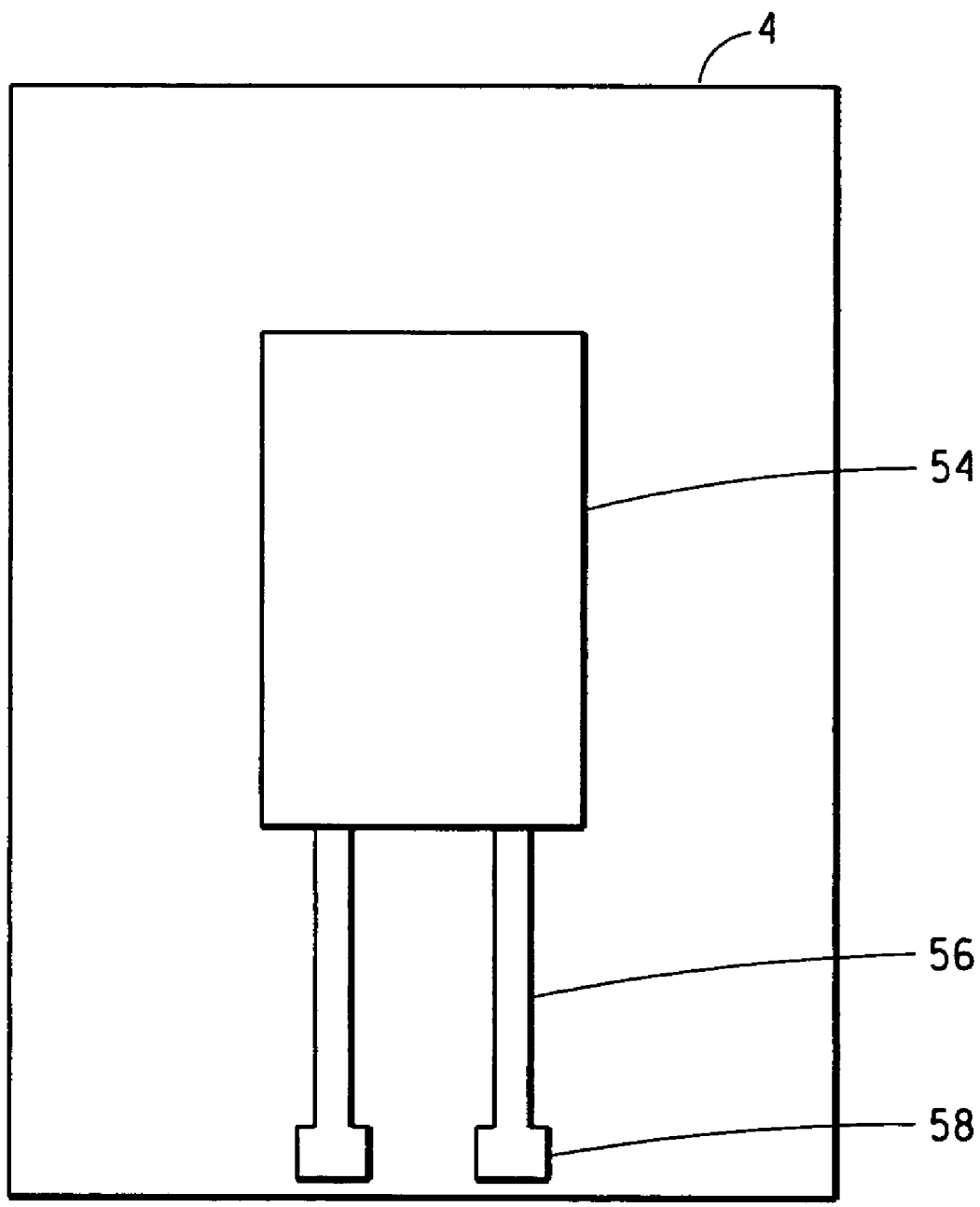
FIG. 4 shows a layout of a heater on a substrate in an apparatus for analyzing a mixture of gases.

In the apparatus of this invention, when sensor elements are located on a surface of a substrate as described above, it is possible if desired to locate a heater on another surface of the substrate. FIG. 4 shows an example of a layout for a heater. In FIG. 4, a heater 54 on a surface of a substrate 4 is connected to electrodes 56, which are in turn connected to contact terminals 58. The heater may, for example, be a heating plate, may be made of metals such as gold, platinum or palladium or a mixture of two or more thereof, and may be deposited by printing or other known techniques.

When sensor elements are located on one surface of a substrate, and a heater is located on another surface of the substrate, there will be in the apparatus of the invention electrodes on both surfaces of the substrate. As shown by comparing FIGS. 1 through 3 with FIG. 4, it is seen that there may be at least twice as many, or at least three times as many, electrodes on a first surface of the substrate as there are on the second surface.

As described above, in the apparatus of this invention, sensor elements may be located on one or more surfaces of a substrate. Particularly in the case of a multi-layer laminate, sensor elements may be located on two or more surfaces. The materials that are used as the sensor elements may be deposited on different layers of "green" tape before the various layers are assembled into the final, cured laminate that constitutes the substrate. The layers on which the sensor elements are located become surfaces of the substrate.

Electrodes may be deposited on the same layers as the sensor elements, or may be deposited on layers that are on the interior of the substrate and that thus do not become surfaces. Electrodes may thus be located on one, two or more of the surfaces of the substrate, or on none of the surfaces. Moreover, as sensor elements may be located on one, two or more surfaces of the substrate, each of the embodiments as shown in FIGS. 1, 2 and 3 may be located on a surface of a substrate. As a result, there may be 4 or more, 6 or more, 8 or more or 10 or more sensor elements on one, two or more surfaces of a substrate. The substrate may thus contain in total 6 or more, 8 or more, 10 or more or 12 or more sensor elements.

A further alternative embodiment is shown in FIG. 3, in which the same numbering for the features shown in FIG. 1 is continued in FIG. 3 where those same features are also shown, in FIG. 3. In FIG. 3, Sensor Element A-1 12 is contacted by a first electrode, Electrode A 10, and a second electrode, Electrode K 52. Sensor Element A-2 14 is also contacted by Electrode A 10, and Sensor Element B-1 18 is also contacted by Electrode K 52. Electrode A 10 thus contacts at least one member of the group consisting of Sensor Elements A-1 12, A-2 14 and A-3 22; as does Electrode K 52. Although Sensor Element B-2 20 is not contacted by Electrode K 52, Electrode K 52 nevertheless also contacts at least one member of the group consisting of Sensor Elements B-1 18, B-2 20 and B-3 24. No member of the group consisting of Sensor Elements A-1 12, A-2 14 and A-3 22 is a member of the group consisting of Sensor Elements B-1 18, B-2 20 and B-3 24.

It may also be seen in FIG. 53 that Electrode A not only contacts more than one member of the group consisting of Sensor Elements A-1 12, A-2 14 and A-3 22, it contacts each member of that group.

A further alternative embodiment is shown in FIG. 3, in which the apparatus contains sensor elements and electrodes in addition to those described in the above embodiment as also shown in FIG. 3. The same numbering for the features of both embodiments shown in FIG. 3 is continued. In FIG. 3, Electrode K 52 contacts Sensor Element E-1 32, and thus contacts at least one member of the group consisting of Sensor Elements E-1 32, E-2 34 and E-3 36. No member of the group consisting of Sensor Elements E-1 32, E-2 34 and E-3 36 is a member of either of the groups consisting respectively of Sensor Elements A-1 12, A-2 14 and A-3 22; and B-1 18, B-2 20 and B-3 24.

A third electrode, Electrode B 16, contacts Sensor Elements B-1 18 and B-2 20, and it thus may be seen in FIG. 63 that Electrode B 16 contacts at least one member of the group consisting of Sensor Elements B-1 18, B-2 20 and B-3 24. It may also be seen, however, that Electrode B 16 contacts more than one member of that group, and actually contacts each member of that group. A fourth electrode, Electrode J 50, contacts at least one member of the group consisting of Sensor Elements B-1 18, B-2 20 and B-3, and at least one member of the group consisting of Sensor Elements E-1 32, E-2 34 and E-3 36.

A further alternative embodiment is shown in FIG. 3, in which the apparatus contains sensor elements and electrodes in addition to those described in the above embodiments. The same numbering for the features all embodiments shown in FIG. 3 is continued. In FIG. 3, a fifth electrode, Electrode E 30, contacts at least one member of the group consisting of Sensor Elements E-1 32, E-2 34 and E-3 36. It may also be seen, however, that Electrode E 30 contacts more than one member of that group, and actually contacts each member of that group.

Electrode K 52 contacts at least one member of the group consisting of Sensor Elements G-1 42, G-2 44 and G-3 46. No member the group consisting of Sensor Elements G-1 42, G-2 44 and G-3 46 is a member of any of the groups consisting, respectively, of Sensor Elements A-1 12, A-2 14 and A-3 22; B-1 18, B-2 20 and B-3 24; and E-1 32, E-2 34 and E-3 36. A sixth electrode, Electrode G 40 also contacts at least one member of the group consisting of Sensor Elements G-1 42, G-2 44 and G-3 46. It may also be seen, however, that Electrode G 40 contacts more than one member of that group, and actually contacts each member of that group.

As is true of other embodiments this apparatus, some or all of these groups of sensor elements may be located on one surface of a substrate, and a heater, as described above, may be located on another surface of the substrate. In such case, electrodes will be located on both surfaces of the substrate. There may be at least twice as many, or at least three times as many, electrodes on a first surface of the substrate as there are on the second surface.

Also as described above, sensor elements may be located on one or more surfaces of a substrate. Particularly in the case of a multi-layer laminate, sensor elements may also be located on two or more surfaces. As a result, there may be 4 or more, 6 or more, 8 or more or 10 or more sensor elements on one, two or more surfaces of a substrate. The substrate may thus contain in total 6 or more, 8 or more, 10 or more or 12 or more sensor elements. Electrodes may be deposited on the same surfaces as the sensor elements, or may be located on the interior of the substrate. Electrodes may thus be located on one, two or more of the surfaces of the substrate, or on none of the surfaces.

Other descriptions of the apparatus of this invention, and of methods of use thereof, may be found in U.S. application Ser. No. 09/977,791, filed on Oct. 15, 2001, and in U.S. application Ser. No. 10/117,472, filed on Apr. 5, 2002, each of which is incorporated in its entirety as a part hereof for all purposes.

Where the apparatus of this invention is stated or described as comprising, including, containing or having certain features, integers and/or components, it is to be understood, unless the statement or description explicitly provides to the contrary, that one or more components other than those explicitly stated or described may be present in the apparatus. In an alternative embodiment, however, the apparatus of this invention may be stated or described as consisting essentially of certain components, in which embodiment components that would materially alter the principle of operation or the distinguishing characteristics of the apparatus are not present therein. In a further alternative embodiment, the apparatus of this invention may be stated or described as consisting of certain components, in which embodiment components other than those as stated are not present therein.

Where the indefinite article "a" or "an" is used with respect to a statement or description of the presence of a component in the apparatus of this invention, it is to be understood, unless the statement or description explicitly provides to the contrary, that the use of such indefinite article does not limit the presence of the component in the apparatus to one in number.

What is claimed is:

1. A gas-sensitive apparatus comprising
   (a) first, second, third and fourth groups of sensor elements wherein no member of one group of sensor elements is a member of any other group of sensor elements;
   (b) a first electrode that contacts each member of the first group of sensor elements;
   (c) a second electrode that contacts one member of each of the four groups of sensor elements;
   (d) a third electrode that contacts each member of the second group of sensor elements;
   (e) a fourth electrode that contacts a member of the second group of sensor elements that is different from the member contacted by the second electrode, and a member of the third group of sensor elements that is different from the member contacted by the second electrode;
   (f) a fifth electrode that contacts each member of the third group of sensor elements;
   (g) a sixth electrode that contacts each member of the fourth group of sensor elements;
   (h) a seventh electrode that contacts a member of the first group of sensor elements that is different from the member contacted by the second electrode;
   (i) an eighth electrode that contacts a member of the second group of sensor elements that is different from the member contacted by the second electrode;
   (j) a ninth electrode that contacts a member of the third group of sensor elements that is different from the member contacted by the second electrode; and
   (k) a tenth electrode that contacts a member of the fourth group of sensor elements that is different from the member contacted by the second electrode.

2. An apparatus according to claim 1 that comprises at least 8 sensor elements.

3. An apparatus according to claim 1 that is a unitary body.

4. An apparatus according to claim 1 that is a multi-layer laminate.

5. An apparatus according to claim 1 that has a plurality of surfaces, and wherein sensor elements are located on more than one of the surfaces.

6. An apparatus according to claim 5 wherein at least four sensor elements are located on each of two surfaces.

7. An apparatus according to claim 1 that has a plurality of surfaces, and wherein electrodes are located on at least one surface.

8. An apparatus according to claim 1 wherein the sensor elements are located on one or more surfaces of a substrate that has a plurality of surfaces, wherein electrodes are located in interior layers of the substrate.

9. An apparatus according to claim 1 that may be passed through a circle having a diameter of no more than about 50 mm.

10. An apparatus according to claim 1 that may be passed through a circle having a diameter of no more than about 18 mm.

* * * * *